United States Patent
Dhake et al.

(10) Patent No.: US 12,422,423 B2
(45) Date of Patent: Sep. 23, 2025

(54) METHOD OF MEASURING BENZIMIDAZOLE-BASED COMPOUNDS IN WATER

(71) Applicant: ECOLAB USA INC., St. Paul, MN (US)

(72) Inventors: Kishor Padmakar Dhake, Nashik (IN); Anup Pandurang Thakur, Jalgaon (IN); James Joseph Michels, Naperville, IL (US)

(73) Assignee: Ecolab USA Inc., St. Paul, MN (US)

( * ) Notice: Subject to any disclaimer, the term of this patent is extended or adjusted under 35 U.S.C. 154(b) by 1378 days.

(21) Appl. No.: 16/281,877

(22) Filed: Feb. 21, 2019

(65) Prior Publication Data

US 2019/0271674 A1 Sep. 5, 2019

Related U.S. Application Data (60) Provisional application No. 62/636,928, filed on Mar. 1, 2018.

(51) Int. Cl.
| | |
|---|---|
| *G01N 33/18* | (2006.01) |
| *C23F 11/14* | (2006.01) |
| *G01N 21/64* | (2006.01) |

(52) U.S. Cl.
CPC ............ *G01N 33/18* (2013.01); *C23F 11/149* (2013.01); *G01N 21/64* (2013.01)

(58) Field of Classification Search
CPC ...... G01N 33/18; G01N 21/64; G01N 21/643; G01N 21/78; G01N 31/22; G01N 2201/129; G01N 33/1826; C23F 11/149
See application file for complete search history.

(56) References Cited

U.S. PATENT DOCUMENTS

| | | | |
|---|---|---|---|
| 4,696,763 | A | 9/1987 | Bentley et al. |
| 4,783,314 | A | 11/1988 | Hoots et al. |
| (Continued) | | | |

FOREIGN PATENT DOCUMENTS

| | | |
|---|---|---|
| EP | 0566902 | 10/1993 |
| JP | H0657460 A | 3/1994 |
| (Continued) | | |

OTHER PUBLICATIONS

Novo, M. et al. "Influence of Acidity on the Fluorescence Spectra of 2-Pyridylbenzimidazoles in Aqueous Solution," J. Chem. Soc. Faraday Trans. 1993, 86(6), 885-889 (Year: 1993).*

(Continued)

*Primary Examiner* — Jennifer Wecker
*Assistant Examiner* — Michelle Adams
(74) *Attorney, Agent, or Firm* — Eric D. Babych; Barnes & Thornburg LLP (57) ABSTRACT

The present disclosure generally relates to methods of measuring benzimidazole-based corrosion inhibitors in cooling water. Methods may include withdrawing a sample of water containing a benzimidazole-based compound from an aqueous system and adding an acid to the sample of water and/or diluting with water. Methods may also include exposing the sample of water to light energy of a selected excitation wavelength and measuring an intensity of emitted light about a selected fluorescence emission wavelength. The intensity of the emitted light may be compared to a standard curve, which can be a plot of fluorescence emission intensity of the benzimidazole-based compound versus concentration of the benzimidazole-based compound. The concentration of the benzimidazole-based compound in the sample of water may be determined from the standard curve.

20 Claims, 5 Drawing Sheets

Substituted Benzimidazole spiked in various Hardness Concentrations

(56) References Cited

U.S. PATENT DOCUMENTS

| | | | |
|---|---|---|---|
| 5,242,602 A * | 9/1993 | Richardson | G01N 33/1813 436/171 |
| 5,278,074 A | 1/1994 | Rao et al. | |
| 5,389,548 A | 2/1995 | Hoots et al. | |
| 6,369,894 B1 | 4/2002 | Rasimas et al. | |
| 7,099,012 B1 | 8/2006 | Crawford et al. | |
| 8,248,611 B2 | 8/2012 | Christensen et al. | |
| 8,352,207 B2 | 1/2013 | Tokhtuev et al. | |
| 8,373,140 B2 | 2/2013 | Tokhtuev et al. | |
| 9,557,270 B2 | 1/2017 | Tokhtuev et al. | |
| 9,618,450 B2 | 4/2017 | Banks et al. | |
| 9,908,877 B2 | 3/2018 | Hutt et al. | |
| 9,970,045 B2 * | 5/2018 | Wu | G01N 33/5094 |
| 11,275,071 B2 * | 3/2022 | Schwabacher | C09B 29/0014 |
| 2006/0262309 A1 | 11/2006 | Banks | |
| 2009/0212236 A1 | 8/2009 | Tokhtuev et al. | |
| 2011/0240886 A1 | 10/2011 | Tokhtuev et al. | |
| 2011/0240887 A1 | 10/2011 | Christensen et al. | |
| 2011/0242539 A1 | 10/2011 | Christensen et al. | |
| 2011/0246118 A1 | 10/2011 | Tokhtuev et al. | |
| 2013/0233804 A1 | 9/2013 | Xie et al. | |
| 2015/0152329 A1 | 6/2015 | Seetharaman et al. | |
| 2016/0047746 A1 | 2/2016 | Tokhtuev et al. | |
| 2016/0097721 A1 | 4/2016 | Bolduc et al. | |
| 2016/0103089 A1 | 4/2016 | Boyette et al. | |
| 2016/0348251 A1 | 12/2016 | Seetharaman et al. | |
| 2016/0348252 A1 | 12/2016 | Rane et al. | |
| 2017/0356093 A1 * | 12/2017 | Kalakodimi | C23F 11/149 |

FOREIGN PATENT DOCUMENTS

| | | |
|---|---|---|
| JP | H09178662 A | 7/1997 |
| JP | 2017501302 A | 1/2017 |
| TW | 201029650 | 8/2010 |
| WO | 2017066672 A1 | 4/2017 |

OTHER PUBLICATIONS

Marinescu, M. "Recent advances in the use of benzimidazoles as corrosion inhibitors," BMC Chemistry 13, 136 (2019) (Year: 2019).*

Petrović Mihajlović, Marija B. et al, "Copper Corrosion Inhibitors. Period 2008-2014. A Review," International Journal of Electrochemical Science, 2015, 10, pp. 1027-1053.

Li, PhD, "Thesis Simultaneous Analysis of Three Benzimidazole" Sep. 2, 2017, English abstract.

Abboud, Y. et al., "2-(o-Hydroxyphenyl)Benzimidazole as a New Corrosion Inhibitor for mild Steel in Hydrochloric Acid Solution" Int. J. Electrochem. Sci. (2012) 7: 2543-2551.

Berezin, Mikhall Y., "pH-Dependent Optical Properties of Synthetic Fluorescent Imidazoles" Chemistry (2009) 15(14): 3560-3566.

Chipem, Francis A. S. et al. "Role of nitrogen substitution in phenyl ring on excited state intramolecular proton transfer and rotamerism of 2-(2-hydroxyphenyl)benzimidazole: A theoretical study" The Journal Of Chemical Physics (2011) 134: 104308-1 thru 104308-9.

He, Chengjun et al., "Inhibition Effect of Environment-Friendly Inhibitors on the Corrosion of Carbon Steel in Recirculating Cooling Water" Industrial & Engineering Chemistry Research (2015) 54: 1971-1981.

Hoffmann, H.S. et al., "Fluorescent silica hybrid materials containing benzimidazole dyes obtained by sol-gel method and high pressure processing" Materials Chemistry and Physics (2011) 126: 97-101.

Hsieh, M.K. et al., "Effect of Tolyltriazole on the Corrosion Protection of Copper against Ammonia and Disinfectants in Cooling Systems" Ind. Eng. Chem. Res. (2010) 49: 7313-7322.

Khaled, K.F., "Studies of iron corrosion inhibition using chemical, electrochemical and computer simulation techniques" Electrochimica Acta (2010) 55: 6523-6532.

Li, Yuanzhen et al., "Determination of benzotriazole in industrial cooling water by fluorescence" Instrumentation Science & Technology (2017) 45(3): 290-300.

Omar, A. F. B. et al., "Turbidimeter Design and Analysis: A Review on Optical Fiber Sensors for the Measurement of Water Turbidity" Sensors (2009) 9: 8311-8335.

Ravichandran, K. et al., "Mannich Base Derivatives—A Novel Class of Corrosion Inhibitors for Cooling Water Systems" Corrosion Reviews (2001) 19(1): 29-42.

Rodembusch, F.S. et al., "New fluorescent monomers and polymers displaying an intramolecular proton-transfer mechanism in the electronically excited state (ESIPT) Part II. Synthesis, spectroscopic characterization and solvatochromism of new benzazolylvinylene derivatives" Journal of Photochemistry and Photobiology A: Chemistry (2005) 173: 81-92.

International Search Report and Written Opinion for corresponding International Application PCTUS2019018889; Jun. 12, 2019; 23 pages.

Kondo et al., Fluorescence Spectra of Some Benzimidazoles in Acid Media. Bulletin of the Chemical Society of Japan, 1969, vol. 42, pp. 1433-1435.

* cited by examiner

METHOD OF MEASURING BENZIMIDAZOLE-BASED COMPOUNDS IN WATER

BACKGROUND

1. Field of the Invention

The present disclosure generally relates to methods of measuring benzimidazole based corrosion inhibitors in cooling water.

2. Description of the Related Art

Fluorometric spectroscopy concerns detection of fluorescent light emitted by a sample of interest. It involves using a beam of light, usually ultraviolet (UV) light, that excites the electrons in molecules of certain compounds in the sample and causes them to emit light of a lower energy. This lower energy light is typically, but not necessarily, visible light. This technique is popular in biochemical and medical applications, such as confocal microscopy, fluorescence resonance energy transfer and fluorescence lifetime imaging. Molecular fluorescence spectroscopy instrumentation generally consists of a source of excitation radiant energy, an excitation wavelength selector, a sample cell to contain the analyte material, an emission wavelength selector, a detector with signal processor and a readout device.

There are several types of fluorometers for measuring fluorescence. Filter fluorometers use optical filters to isolate the incident light and fluorescent light. Spectrofluorometers use diffraction grating monochromators to isolate the incident light and fluorescent light. In these devices, the spectrum consists of the intensity of emitted light as a function of the wavelength of either the incident light (excitation spectrum) or the emitted light, or both.

BRIEF SUMMARY

In some embodiments, a method of determining corrosion inhibitor concentration in water is disclosed. The method can include withdrawing a sample of water from an aqueous system, the sample of water comprising a benzimidazole-based compound. The method can include adding an acid to the sample of water; exposing the sample of water to light energy of a selected excitation wavelength; measuring an intensity of emitted light about a selected fluorescence emission wavelength; comparing the intensity of the emitted light to a standard curve, the standard curve comprising a plot of fluorescence emission intensity of the benzimidazole-based compound versus concentration of the benzimidazole-based compound; and determining the concentration of the benzimidazole-based compound in the sample of water from the standard curve.

In some embodiments, the method can include diluting the sample of water by adding water to the sample of water.

In some embodiments, the sample of water is diluted by about 10 times.

In some embodiments, the aqueous system is a cooling water system and the sample of water is a sample of cooling tower water.

In some embodiments, the sample of water can include hard water.

In some embodiments, the sample of water can include about 25 ppm to about 400 ppm of calcium and about 25 ppm to about 400 ppm of magnesium.

In some embodiments, the benzimidazole-based compound is of formula (I) or a salt thereof, (I)

where $R^1$ is halo, hydrogen, deuterium, hydroxyl, carbonyl, substituted or unsubstituted $C_1$-$C_{16}$ alkyl, substituted or unsubstituted $C_4$-$C_6$ aryl, substituted or unsubstituted $C_2$-$C_{16}$ alkenyl, substituted or unsubstituted $C_2$-$C_{16}$ alkynyl, substituted or unsubstituted $C_4$-$C_6$ heteroaryl, or substituted or unsubstituted $C_3$-$C_8$ cycloalkyl; X is hydrogen, $CR^2R^3Y$, or $NR^2R^3Y$; Y is hydroxyl, halo, oxo, substituted or unsubstituted $C_1$-$C_{16}$ alkoxy, thiol, alkylthio, amino, hydrogen, or aminoalkyl; $R^2$ and $R^3$ are each independently selected from the group consisting of: hydrogen, halo, hydroxyl, substituted or unsubstituted $C_4$-$C_6$ aryl, substituted or unsubstituted $C_4$-$C_6$ heteroaryl, carbonyl, substituted or unsubstituted $C_2$-$C_{16}$ alkenyl, substituted or unsubstituted $C_2$-$C_{16}$ alkynyl, substituted or unsubstituted $C_3$-$C_8$ cycloalkyl, and substituted or unsubstituted $C_1$-$C_{16}$ alkyl; and $R^4$, $R^5$, $R^6$, and $R^7$ are each independently selected from the group consisting of: hydrogen, halo, amino, cyano, substituted or unsubstituted $C_1$-$C_{16}$ alkoxy, hydroxyl, thiol, carbonyl, nitro, phosphoryl, phosphonyl, sulfonyl, substituted or unsubstituted $C_1$-$C_{16}$ alkyl, substituted or unsubstituted $C_4$-$C_6$ aryl, substituted or unsubstituted $C_2$-$C_{16}$ alkenyl, substituted or unsubstituted $C_2$-$C_{16}$ alkynyl, substituted or unsubstituted $C_4$-$C_6$ heteroaryl, and substituted or unsubstituted $C_3$-$C_8$ cycloalkyl.

In some embodiments, the benzimidazole-based compound is of formula (II) or salt thereof, (II)

where $R^1$ is hydrogen, a substituted or unsubstituted $C_1$-$C_{16}$ alkyl group, or a substituted or unsubstituted $C_4$-$C_6$ aryl group; $R^8$ is a bond or $CHR^9$; $R^9$ is hydrogen, halo, $NR^{10}R^{11}$, or $OR^{10}$; wherein $R^{10}$ and $R^{11}$ are each independently selected from the group consisting of: hydrogen, a substituted or unsubstituted $C_1$-$C_{12}$ alkyl group, and a substituted or unsubstituted $C_4$-$C_6$ aryl group; and Z is independently nitrogen, $CR^4$, or $NR^{10}$.

In some embodiments, Z is $CR^4$ and $R^4$ is hydrogen.

In some embodiments, the benzimidazole-based compound is selected from the group consisting of:

In some embodiments, the acid is a mineral acid, an organic acid, or any combination thereof.

In some embodiments, the acid is hydrochloric acid, formic acid, phosphoric acid, nitric acid, sulfuric acid, acetic acid, propionic acid, oxalic acid, lactic acid, citric acid, or any combination thereof.

In some embodiments, the selected excitation wavelength is from about 200 nm to about 400 nm.

In some embodiments, the selected fluorescence emission wavelength is from about 300 nm to about 500 nm.

In some embodiments, the method can includes protonating the benzimidazole-based compound.

In some embodiments, the sample of water has a pH of about 1 to about 5 after adding the acid.

In some embodiments, the acid is added to the sample of water in an amount of about 0.001% by weight to about 10% by weight.

In some embodiments, the addition of the acid decreases a fluorescence intensity of an emission band at 300 nm and increases a fluorescence intensity of an emission band at 370 nm for the benzimidazole-based compound.

In other embodiments, a method of controlling the concentration of a corrosion inhibitor in an aqueous system is disclosed. The method can include determining the concentration of the benzimidazole-based compound in the sample of water; and adding the benzimidazole-based compound to the aqueous system if the concentration of the benzimidazole-based compound in the sample of water is below a predetermined level.

In some embodiments, the predetermined level is from about 0.05 ppm to about 20 ppm.

In some embodiments, the aqueous system can include an oxidizing biocide.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE DRAWINGS

A detailed description of the invention is hereafter described with specific reference being made to the drawings in which.

DETAILED DESCRIPTION

Various embodiments are described below. The relationship and functioning of the various elements of the embodiments may better be understood by reference to the following detailed description. However, embodiments are not limited to those illustrated below. In certain instances, details may have been omitted that are not necessary for an understanding of embodiments disclosed herein.

In some embodiments, a method of determining corrosion inhibitor concentration in water is disclosed. The method may include withdrawing a sample of water from an aqueous system. The sample of water may contain a benzimidazole-based compound. The method may include adding an acid to the sample of water; exposing the sample of water to light energy of a selected excitation wavelength; measuring an intensity of emitted light about a selected fluorescence emission wavelength; and comparing the intensity of the emitted light to a standard curve. The standard curve can be a plot of fluorescence emission intensity of the benzimidazole-based compound versus concentration of the benzimidazole-based compound. The method may include determining the concentration of the benzimidazole-based compound in the sample of water from the standard curve.

In some embodiments, the method may include diluting the sample of water by adding water to the sample of water. In some embodiments, the sample of water is diluted by adding a liquid consisting of water to the sample of water. The sample of water can be diluted before or after the acid is added. When water is added to the sample of water after adding the acid, the sample of water is diluted before exposing the sample of water to light energy of a selected wavelength. In some embodiments, the sample of water is diluted by about 10 times. In some embodiments, the sample of water is diluted by about 10 times to about 20 times. In some embodiments, the sample of water is diluted by about 11 times, about 12 times, about 13 times, about 14 times, about 15 times, about 16 times, about 17 times, about 18 times, or about 19 times.

Diluting the sample of water is especially advantageous when the sample of water includes hard water or any other substances which can interfere in fluorescence assay such as any other substances with fluorescence properties. Hard water and many other cooling water substances can interfere with the fluorescence measurements of the benzimidazole-based compound leading to inaccurate conclusions of the compound concentration. Hard water, as used herein, refers to water having moderate to high mineral content of about 60 ppm to about 7000 ppm. In some embodiments, the sample of water may include about 25 ppm to about 400 ppm of calcium and about 25 ppm to about 400 ppm of magnesium. Other substances may include any other organic molecules with fluorescence properties either in free form or tagged on other substances.

Cooling water typically contains elevated levels of calcium, magnesium, copper, iron, free chlorine, turbidity, and many other parameters which can interfere in fluorometric assay. A high concentration of these ions can quench fluorescence and reduce the specificity of assay. The methods of the present disclosure are especially suited for determining benzimidazole concentration in cooling water. In some embodiments, the aqueous system is a cooling water system and the sample of water is a sample of cooling tower water. The cooling water can contain copper (up to about 5 ppm), iron (up to about 5 ppm), calcium (up to about 50 ppm), magnesium (up to about 50 ppm), free chlorine (up to about 5 ppm), and have a turbidity of up to about 100 NTU.

The benzimidazole-based compound can be a compound of formula (I) or salt thereof or a compound of formula (II) or salt thereof, where $R^1$ is halo, hydrogen, deuterium, hydroxyl, carbonyl, substituted or unsubstituted $C_1$-$C_{16}$ alkyl, substituted or unsubstituted $C_4$-$C_6$ aryl, substituted or unsubstituted $C_2$-$C_{16}$ alkenyl, substituted or unsubstituted $C_2$-$C_{16}$ alkynyl, substituted or unsubstituted $C_4$-$C_6$ heteroaryl, or substituted or unsubstituted $C_3$-$C_8$ cycloalkyl.

"Alkoxy" refers to a moiety of the formula RO—, where R is alkyl, alkenyl, or alkynyl.

"Alkyl" refers to a straight-chain or branched alkyl substituent. Examples of such substituents include methyl, ethyl, propyl, isopropyl, n-butyl, sec-butyl, isobutyl, tert-butyl, pentyl, isoamyl, hexyl, and the like.

"Alkylthio" refers to a moiety of the formula RS—, where R is alkyl, aryl, alkenyl, or alkynyl.

"Aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2n electrons, according to Huckel's Rule.

"Carbonyl" refers to a substituent comprising a carbon double bonded to an oxygen. Examples of such substituents include aldehydes, ketones, carboxylic acids, esters, amides, and carbamates.

"Cycloalkyl" refers to a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups, such as methyl groups, ethyl groups, and the like.

"Halo" refers to a fluoro group, chloro group, bromo group, or iodo group.

"Heteroaryl" refers to a monocyclic or bicyclic 5- or 6-membered ring system, wherein the heteroaryl group is unsaturated and satisfies Huckel's rule. Non-limiting examples of heteroaryl groups include furanyl, thiophenyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, quinazolinyl, and the like.

"Oxidizing Halogen" refers to a form of the halogen capable of performing oxidizing reactions in aqueous systems.

"Oxo" refers to an oxygen atom double-bonded to a carbon atom.

Compounds of the present disclosure may be substituted with suitable substituents. The term "suitable substituent," as used herein, is intended to mean a chemically acceptable functional group, preferably a moiety that does not negate the activity of the compounds. Such suitable substituents include, but are not limited to, halo groups, perfluoroalkyl groups, perfluoro-alkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C═O)— groups, heterocylic groups, cycloalkyl groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxy-carbonyl groups, alkylsulfonyl groups, and arylsulfonyl groups. In some embodiments, suitable substituents may include halogen, an unsubstituted $C_1$-$C_{12}$ alkyl group, an unsubstituted $C_4$-$C_6$ aryl group, or an unsubstituted $C_1$-$C_{10}$ alkoxy group. Those skilled in the art will appreciate that many substituents can be substituted by additional substituents.

In some embodiments, $R^1$ is hydrogen, a substituted or unsubstituted $C_1$-$C_{16}$ alkyl group, or a substituted or unsubstituted $C_4$-$C_6$ aryl group.

In some embodiments, $R^1$ is hydrogen.

In some embodiments, $R^2$ and $R^3$ are each independently selected from the group consisting of: hydrogen, halo, hydroxyl, substituted or unsubstituted $C_4$-$C_6$ aryl, substituted or unsubstituted $C_4$-$C_6$ heteroaryl, carbonyl, substituted or unsubstituted $C_2$-$C_{16}$ alkenyl, substituted or unsubstituted $C_2$-$C_{16}$ alkynyl, substituted or unsubstituted $C_3$-$C_6$ cycloalkyl, and substituted or unsubstituted $C_1$-$C_{16}$ alkyl. In some embodiments, $R^2$ and $R^3$ are each independently selected from the group consisting of: hydrogen, halo, hydroxyl, substituted or unsubstituted $C_4$-$C_6$ aryl, substituted or unsubstituted $C_4$-$C_6$ heteroaryl, carbonyl, and substituted or unsubstituted $C_1$-$C_{16}$ alkyl. In some embodiments, $R^2$ and $R^3$ are each independently selected from the group consisting of: hydrogen and substituted or unsubstituted $C_4$-$C_6$ aryl. In some embodiments, $R^2$ is substituted or unsubstituted $C_4$-$C_6$ aryl, and $R^3$ is hydrogen.

In some embodiments, the benzimidazole-based compound can be a compound of formula (III) or any salt thereof.

(III)

In some embodiments, $R^4$, $R^5$, $R^6$, and $R^7$ are each independently selected from the group consisting of: hydrogen, halo, amino, aminoalkyl, cyano, substituted or unsubstituted $C_1$-$C_{16}$ alkoxy, hydroxyl, thiol, carbonyl, nitro, phosphoryl, phosphonyl, sulfonyl, substituted or unsubstituted $C_1$-$C_{16}$ alkyl, substituted or unsubstituted $C_4$-$C_6$ aryl, substituted or unsubstituted $C_2$-$C_{16}$ alkenyl, substituted or unsubstituted $C_2$-$C_{16}$ alkynyl, substituted or unsubstituted $C_4$-$C_6$ heteroaryl, and substituted or unsubstituted $C_3$-$C_8$ cycloalkyl. In some embodiments, at least one of $R^4$, $R^5$, $R^6$, and $R^7$ is hydrogen. In some embodiments, $R^4$, $R^5$, and $R^7$ are each hydrogen. In some embodiments, $R^4$ is hydrogen. In some embodiments, $R^5$ is hydrogen. In some embodiments, $R^6$ is hydrogen. In some embodiments, $R^7$ is hydrogen.

In some embodiments, $R^6$ is substituted or unsubstituted $C_1$-$C_{16}$ alkyl and $R^4$, $R^5$, and $R^7$ are each hydrogen. In some embodiments, $R^6$ is methyl and $R^4$, $R^5$, and $R^7$ are each hydrogen. In some embodiments, $R^6$ is halo and $R^4$, $R^5$, and $R^7$ are each hydrogen. In some embodiments, $R^6$ is chloro and $R^4$, $R^5$, and $R^7$ are each hydrogen. In some embodiments, $R^6$ is substituted or unsubstituted $C_1$-$C_{16}$ alkyl; $R^5$ is halo; and $R^4$ and $R^7$ are each hydrogen. In some embodiments, $R^6$ is methyl; $R^5$ is bromo; and $R^4$ and $R^7$ are each hydrogen. In some embodiments, $R^4$, $R^5$, $R^6$, and $R^7$ are each hydrogen. Preferably, $R^4$, $R^5$, $R^6$, and $R^7$ are each hydrogen or at least one of $R^4$, $R^5$, $R^6$, and $R^7$ is substituted or unsubstituted $C_1$-$C_{16}$ alkyl and the remaining substituents are hydrogen.

In some embodiments, $R^8$ is a bond or $CHR^9$. In some embodiments, $R^8$ is a bond. In some embodiments, $R^8$ is $CHR^9$. $R^9$ can be hydrogen, halo, $NR^{10}R^{11}$, or $OR^{10}$. In some embodiments, $R^{10}$ and $R^{11}$ are each independently selected from the group consisting of: hydrogen, a substituted or unsubstituted $C_1$-$C_{12}$ alkyl group, and a substituted or unsubstituted $C_4$-$C_6$ aryl group. In some embodiments, $R^8$ is $CHR^9$, $R^9$ is $OR^{10}$, and $R^{10}$ is hydrogen.

In some embodiments, X is hydrogen, $CR^2R^3Y$, or $NR^2R^3Y$. In some embodiments, X is hydrogen. In some embodiments, X is $CR^2R^3Y$. In some embodiments, X is $NR^2R^3Y$.

In some embodiments, X is hydrogen and $R^4$, $R^5$, $R^6$, and $R^7$ are each hydrogen. In some embodiments, X is $CR^2R^3Y$; Y is hydroxyl; and $R^2$ is a substituted or unsubstituted $C_4$-$C_6$ aryl.

In some embodiments, Y is hydroxyl, halo, oxo, substituted or unsubstituted $C_1$-$C_{16}$ alkoxy, thiol, alkylthio, amino, hydrogen, or aminoalkyl. In some embodiments, Y is hydroxyl.

In some embodiments, Z is independently nitrogen, $CR^4$, or $N^+R^{10}$. In some embodiments, Z is $CR^4$. In some embodiments, one Z is nitrogen and the rest are $CR^4$. In some embodiments, at least two Z atoms are nitrogen and the rest are $CR^4$. In some embodiments, Z is $CR^4$ and $R^4$ is hydrogen. In some embodiments, $R^8$ is a bond and at least one Z is nitrogen.

In some embodiments, the compound or salt thereof of formula (I) or formula (II) is

In some embodiments, the compound or salt thereof of formula (I) or formula (II) is

In some embodiments, the compound or salt thereof of formula (I) or formula (II) is

In some embodiments, the compound or salt thereof of formula (I) or formula (II) is

In some embodiments, the compound or salt thereof of formula (I) or formula (II) is

In some embodiments, the compound or salt thereof of formula (I) or formula (II) is

In some embodiments, the compound or salt thereof of formula (I) or formula (II) is

In some embodiments, the compound or salt thereof of formula (I) or formula (II) is

In some embodiments, the compound or salt thereof of formula (I) or formula (II) is

In some embodiments, the compound or salt thereof of formula (I) or formula (II) is In some embodiments, the compound or salt thereof of formula (I) or formula (II) is In some embodiments, the compound or salt thereof of formula (I) or formula (II) is In certain embodiments, the salt of the compound of formula (I) may be any salt, such as a chloride salt, bromide salt, iodide salt, sulfate salt, fluoride salt, perchlorate salt, acetate salt, trifluoroacetate salt, phosphate salt, nitrate salt, carbonate salt, bicarbonate salt, formate salt, chlorate salt, bromated salt, chlorite salt, thiosulfate salt, oxalate salt, cyanide salt, cyanate salt, tetrafluoroborate salt, and the like. In some embodiments, salt of the compound of formula (I)-(III) may be a hydrochloride or sulfate salt. The salt form of the compounds can include N-protonated benzimidazole-based compounds with any suitable counter ion.

The acid added to the sample of water can be any acid. The acid can be a mineral acid or an organic acid. For example, the acid can be, but is not limited to, hydrochloric acid, nitric acid, formic acid, sulfuric acid, acetic acid, propionic acid, oxalic acid, lactic acid, phosphoric acid, or any combination thereof. In some embodiments, the acid can be hydrochloric acid, formic acid, or phosphoric acid. In some embodiments, the acid can be formic acid. In some embodiments, an acidic solution can be added to the sample of water, the acidic solution can include any acid and water. The acidic solution can consist of any acid and water.

The amount of acid added to the sample of water is sufficient to protonate a nitrogen atom in the benzimidazole ring. In some embodiments, the acid is added to the sample of water in an amount of about 0.01% by weight to about 2% by weight. In some embodiments, the acid is added to the sample of water in an amount of about 0.01% by weight to about 2% by weight. After adding the acid, the sample of water can have a pH of about 1 to about 5.

In other embodiments, a method of controlling the concentration of a corrosion inhibitor in an aqueous system is provided. The method can include determining the concentration of the benzimidazole-based compound in the sample of water. The step of determining the concentration of the benzimidazole-based compound can include withdrawing a sample of water from an aqueous system; adding an acid to the sample of water; exposing the sample of water to light energy of a selected excitation wavelength; measuring an intensity of emitted light about a selected fluorescence emission wavelength; and comparing the intensity of the emitted light to a standard curve. The standard curve can be a plot of fluorescence emission intensity of the concentration of the benzimidazole-based compound versus concentration of the concentration of the benzimidazole-based compound. Finally, the method can include adding the benzimidazole to the aqueous system if the benzimidazole concentration in the sample of water is below a predetermined level.

The predetermined level can be from about 0.05 ppm to about 20 ppm. In some embodiments, the predetermined level can be from about 0.1 ppm to about 5 ppm. While the compounds of formula (I)-(III) can be added to an aqueous system at any dosage rate, the compounds of formula (I)-(III) are generally added to an aqueous system at a dosage rate of from about 0.01 ppm to about 500 ppm. In certain embodiments, a compound of formula (I)-(III) is added to an aqueous system at a dosage rate of from about 0.01 ppm to about 100 ppm. In certain embodiments, a compound of formula (I)-(III) is added to an aqueous system at a dosage rate of from about 0.01 ppm to about 100 ppm, from about 0.01 ppm to about 75 ppm, from about 0.01 ppm to about 50 ppm, from about 0.01 ppm to about 25 ppm, from about 0.01 ppm to about 10 ppm, from about 0.01 ppm to about 5 ppm, from about 0.1 ppm to about 100 ppm, from about 0.1 ppm to about 75 ppm, from about 0.1 ppm to about 50 ppm, from about 0.1 ppm to about 25 ppm, from about 0.1 ppm to about 10 ppm, from about 0.1 ppm to about 5 ppm, from about 1 ppm to about 100 ppm, from about 1 ppm to about 75 ppm, from about 1 ppm to about 50 ppm, from about 1 ppm to about 25 ppm, from about 1 ppm to about 10 ppm, from about 5 ppm to about 100 ppm, from about 10 ppm to about 100 ppm, from about 25 ppm to about 100 ppm, from about 50 ppm to about 100 ppm, or from about 80 ppm to about 100 ppm.

In some embodiments, the concentration of the compound or salt thereof of formula (I)-(III) in the composition may range from about 1 wt % to about 50 wt %, about 5 wt % to about 50 wt %, about 10 wt % to about 50 wt %, about 15 wt % to about 50 wt %, about 20 wt % to about 50 wt %, about 20 wt % to about 45 wt %, about 25 wt % to about 45 wt %, or about 25 wt % to about 40 wt %. In some embodiments, the composition may include water.

One of skill in the art will appreciate that the dosage of concentration of the benzimidazole-based compound may be outside the disclosed ranges depending on the conditions of the aqueous system and the desired corrosion rate.

In some embodiments, the methods disclosed herein may include measuring a corrosion rate of a metal surface in the aqueous system. Methods of measuring corrosion rates of metal surfaces are well known in the art, and one of ordinary skill in the art would be able to select the appropriate method.

The predetermined corrosion rate may be about 0.2 mpy or less. In certain embodiments, the predetermined corrosion rate is about 0.1 mpy or less, about 0.05 mpy or less, about 0.04 mpy or less, about 0.03 mpy or less, about 0.02 mpy or less, about 0.01 mpy or less, about 0.005 mpy or less, or about 0.002 mpy or less.

In some embodiments, the aqueous system is an industrial water system. "Industrial water system" means any system that circulates or utilizes water as its primary ingredient. Non-limiting examples of "industrial water systems" include cooling systems, boiler systems, heating systems, membrane systems, papermaking systems, or any other systems that circulate or utilize water.

In certain embodiments, the aqueous system is a cooling water system. The cooling water system can be a closed loop cooling water system or an open loop cooling water system.

In some embodiments, the aqueous system may include an oxidizing biocide. In some embodiments, the aqueous system can be chlorinated, brominated, or iodated. In some embodiments, the aqueous system can be chlorinated. An advantage of the disclosed compositions and methods is that compounds of formula (I)-(III) generally provide corrosion protection for metal surfaces in the presence of oxidizing halogens. In certain embodiments, a compound of formula (I)-(III) is added to an aqueous system in contact with a metal surface and provides corrosion protection for metal surface in the presence of any oxidizing halogen compound. In certain embodiments, a compound of formula (I)-(III) inhibits metal corrosion in the presence of oxidizing halogen compounds including, but not limited to, hypochlorite bleach, chlorine, bromine, hypochlorite, hypobromite, chlorine dioxide, iodine/hypoiodous acid, hypobromous acid, halogenated hydantoins, stabilized versions of hypochlorous or hypobromous acids, or combinations thereof. While not wishing to be bound by any particular theory, it is postulated that the relatively large number of heteroatoms of the compounds of formula (I)-(III) provide a greater number of sites for bonding to metal surfaces and metal ions, which can provide enhanced corrosion inhibition as compared to many existing corrosion inhibitors. In addition, it is postulated that the compounds of formula (I)-(III) form stable films because the compounds can form a 1,2-chelation complex with metal.

In certain embodiments, a compound of formula (I)-(III) inhibits metal corrosion when added to an aqueous system comprising a non-halogen-containing oxidizing biocide including, but not limited to, peroxides (e.g., hydrogen peroxide), ozone, persulfates, permanganates, and peracetic acids.

The methods and the compositions of the present disclosure may provide corrosion protection for any metal or metal alloy including, but not limited to, copper, iron, silver, steel (e.g., galvanized steel), zinc alloy, and aluminum. In certain embodiments, the compositions disclosed herein may be added to an aqueous system in contact with a metal surface comprising copper to inhibit metal corrosion. In certain embodiments, the compositions disclosed herein may be added to an aqueous system in contact with a metal surface comprising a copper alloy to inhibit metal corrosion. In certain embodiments, copper complexes with one or more heteroatoms in a compound of formula (I)-(III). In certain embodiments, copper complexes with one or more heteroatoms in a compound of formula (I)-(III). Copper has a wide-range of applications, including use as copper piping and tubing in plumbing and industrial machinery. Copper and copper alloys are well known for their use in cooling water and boiler water systems. In some embodiments, the metal surface may include copper.

The compositions and methods disclosed herein can be used to protect any copper alloy, including bronze and brass. Bronze commonly comprises copper and tin, but may comprise other elements including aluminum, manganese, silicon, arsenic, and phosphorus. Brass comprises copper and zinc, and is commonly used in piping in water boiler systems. In certain embodiments, any of the compositions disclosed herein is added to an aqueous system in contact with a metal surface comprising bronze to inhibit metal corrosion. In certain embodiments, any of the compositions disclosed herein is added to an aqueous system in contact with a metal surface comprising brass, for example admiralty brass, to inhibit metal corrosion. In certain embodiments, any of the compositions disclosed herein is added to an aqueous system in contact with a metal surface comprising a copper-nickel alloy to inhibit metal corrosion.

In certain embodiments, the methods and compositions disclosed herein inhibit the corrosion of mild steel. In certain embodiments, the methods and compositions disclosed herein inhibit the corrosion of metal alloys including, but not limited to, galvanized steel, stainless steel, cast iron, nickel, and combinations thereof. While not wishing to be bound by any particular theory, it is postulated that the compounds of formula (I)-(III) inactivate Cu (II) in solution, preventing the occurrence of galvanic cells on the steel surface.

In some embodiments, the sample of water can include a fluorescent organic compound having an excitation and emission peaks that do not substantially overlap with the benzimidazole-based compound. In certain embodiments, the fluorescent organic compound may be selected from Rhodamine or derivatives thereof, an acridine dye, fluorescein or derivatives thereof, and combinations thereof. The fluorescent organic compound can be a fluorescent tagged polymer.

Those skilled in the art will appreciate that a compound of formula (I)-(III) can be added to an aqueous system alone or in combination with other corrosion inhibitors or treatment chemicals. Multiple corrosion inhibitors can be dosed as a combined corrosion inhibitor formulation or each corrosion inhibitor can be added separately, including two or more compounds of formula (I)-(III). Moreover, a compound of formula (I)-(III) can be added to an aqueous system in combination with a variety of additional corrosion inhibitors including, but not limited to, triazoles, benzotriazoles (e.g., benzotriazole or tolyltriazole), benzimidazoles, orthophosphate, polyphosphates, phosphonates, molybdates, silicates, oximes, and nitrites. The compounds of formulae (I) and (II) also can be added to an aqueous system in combination with a variety of additional additives, such as treatment polymers, anti-microbial agents, anti-scaling agents, colorants, fillers, buffers, surfactants, viscosity modifiers, chelating agents, dispersants, deodorants, masking agents, oxygen scavengers, and indicator dyes.

The methods and compositions disclosed herein can be used to determine the concentration of the benzimidazole-based compound and provide improved control over inhibiting corrosion of metal in an aqueous system. The aqueous system can have any pH.

Table 1 shows a selection of benzimidazole-based compounds that can be detected using the methods disclosed herein and can inhibit corrosion of metals in aqueous systems.

TABLE 1

Compound 1

TABLE 1-continued

Compound 2

Compound 3

Compound 4

Compound 5

Compound 6

Compound 7

TABLE 1-continued

Compound 8

Compound 9

Compound 10

Compound 11

Compound 12

Compound 13

Compound 14

TABLE 1-continued

Compound 15

Compound 16

Compound 17

Compound 18

Compound 19

Compound 20

TABLE 1-continued

Compound 21

One of skill in the art will appreciate that any fluorometer with the appropriate excitation wavelengths and emission filters can be used to measure concentration of the benzimidazole-based compound in the water. For example, the concentration can be measured with any of the fluorometers described in U.S. Pat. Nos. 9,618,450; 9,557,270; 8,373,140; 8,352,207; and 8,248,611, which are each incorporated by reference into the present disclosure.

In some embodiments, a fluorometer according to the disclosure includes an optical sensor. The optical sensor can include a first optical emitter configured to emit light energy of a selected wavelength into a fluid sample under analysis and a second optical emitter configured to emit light energy to measure an amount of scattering in the fluid sample under analysis.

The optical sensor may also include at least one detector that receives fluorescent light emitted from the fluid sample and/or light scattered from the fluid sample. During operation, the detector can detect an amount of fluorescent light emitted from the fluid sample under analysis and the fluorometer can then determine, based on the fluorescent light, a concentration of a fluorescing species in the fluid sample.

Optical sensors are used in a variety of applications, including monitoring industrial processes. An optical sensor can be implemented as a portable, hand-held device that is used to periodically analyze the optical characteristics of a fluid in an industrial process. Alternatively, an optical sensor can be installed online to continuously analyze the optical characteristics of a fluid in an industrial process. In either case, the optical sensor may optically analyze the sample of water and determine different characteristics of the fluid, such as the concentration of one or more chemical species in the fluid.

While the optical sensor can have a variety of different configurations, in some examples, the optical sensor is designed to have a single optical lens through which light is emitted into a fluid sample and also received from the fluid sample. The optical sensor may include a housing that contains various electronic components of the sensor and also has optical pathways to control light movement to and from the single optical lens.

The optical sensor may include an optical detector that is positioned and configured to measure fluorescent emissions emitted by the fluid sample. In some configurations, a single optical detector can be used to measure both scattering and fluorescence from a sample and can receive both scattered and fluoresced light via a single optical pathway in the sensor.

Although the wavelengths can vary, in some examples, the first optical emitter is configured to emit light energy of a wavelength ranging from approximately 200 nm to about 400 nm. The selected excitation wavelength can be from about 230 nm to about 290 nm. In some embodiments, the selected excitation wavelength can be about 280 nm.

To detect light emanating from the sample of water under analysis (e.g., fluorescent emissions, light scattering), the optical sensor includes an optical detector. The optical detector is optically connected to optical pathway and may receive at least a portion of the fluorescent emission beam and the scattered light beam transmitted through the optical window from the sample of water under analysis. Upon the entering housing, the received portions of the fluorescent emission beam and scattered light beam may be directed to the optical detector via the optical pathway for measurement and/or analysis.

The fluorometer can include a light source, such as a UV lamp. The UV lamp may be a gas discharge lamp, a mercury lamp, a deuterium lamp, a metal vapor lamp, a light emission diode or a plurality of light emission diodes.

The selected fluorescence emission wavelength can be from about 300 nm to about 500 nm. In some embodiments, the selected fluorescence emission wavelength can be about 360 nm. The sensor may also measure a reference fluorescence emission of the sample at the first wavelength. The sensor may also measure a fluorescence emission of a zero solution having zero concentration of the benzimidazole-based compound. In that case, the concentration of the chemical in the sample may be calculated based on the calculated difference in the measured fluorescence emission of the sample containing the benzimidazole-based compound and the measured fluorescence emission of the zero solution. The concentration of the sample may also be calculated based on a calibration constant determined for known concentrations of the benzimidazole-based compound in a calibration sample.

For example, when using ultraviolet fluorometric sensing system having a mercury lamp producing a UV radiation at about 280 nm, sample concentrations may be evaluated based upon the signals from two UV detectors. A first detector (fluorescent detector) measures a fluorescent value for the wavelength 360 nm±5 nm (range from 355 nm to 365 nm) and a second detector (reference detector) measures an intensity of UV excitation at a different wavelength.

EXAMPLES

Example 1

Figure 1A:
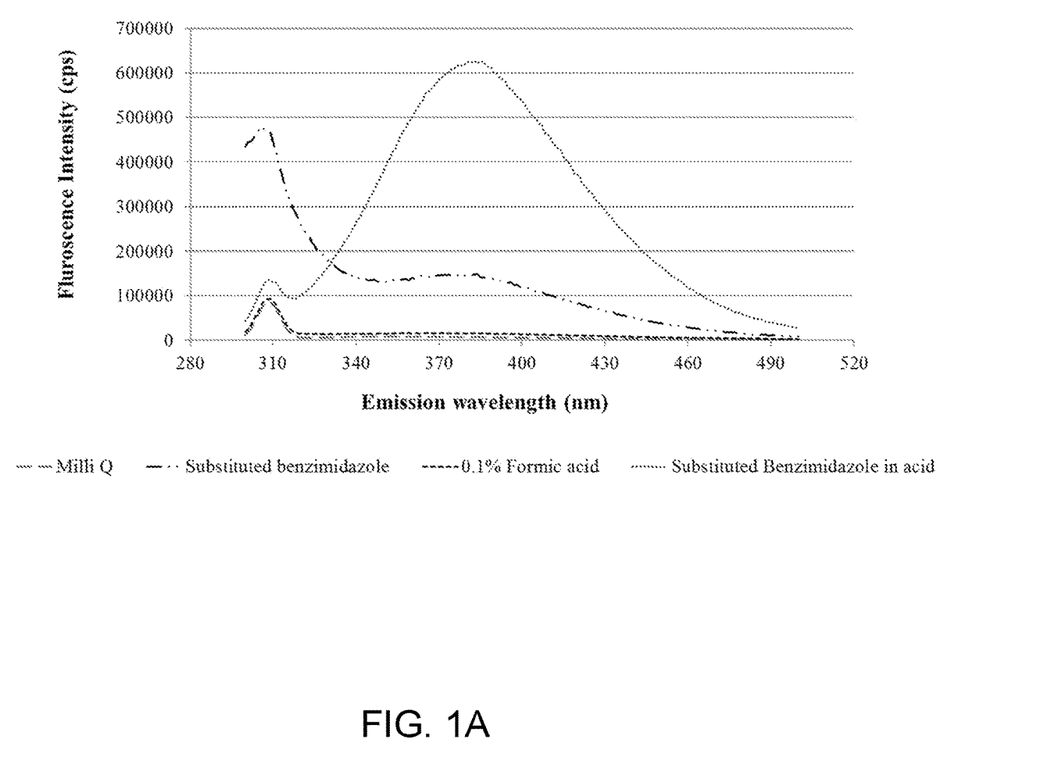
FIG. 1A shows the emission profile for a benzimidazole-based compound in Milli Q water and formic acid.
Figure 1B:
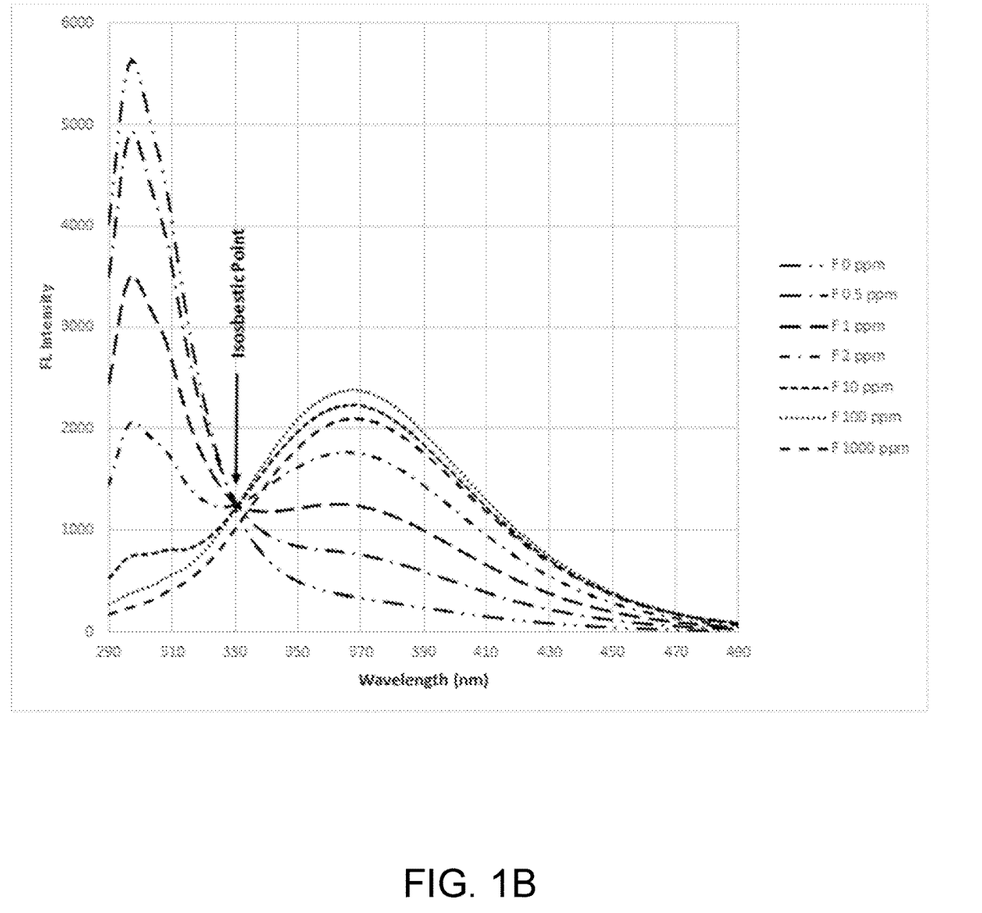
FIG. 1B shows the emission profile for the benzimidazole-based compound in Milli Q water and a different concentration of formic acid.

FIGS. 1A & B show the emission profile for a substituted benzimidazole in Milli Q water and formic acid (FIG. 1A). The substituted benzimidazole in the absence and the presence of formic acid shows two distinct fluorescence intensity emission bands at 300 nm and 370 nm (FIG. 1B). At 330 nm, the isosbestic point was observed. The fluorometer parameters for detection and quantification of the substituted benzimidazole were as follows: excitation=280 nm, emission=360 nm, slit width=5 nm, and voltage=950 V.

Figure 2:
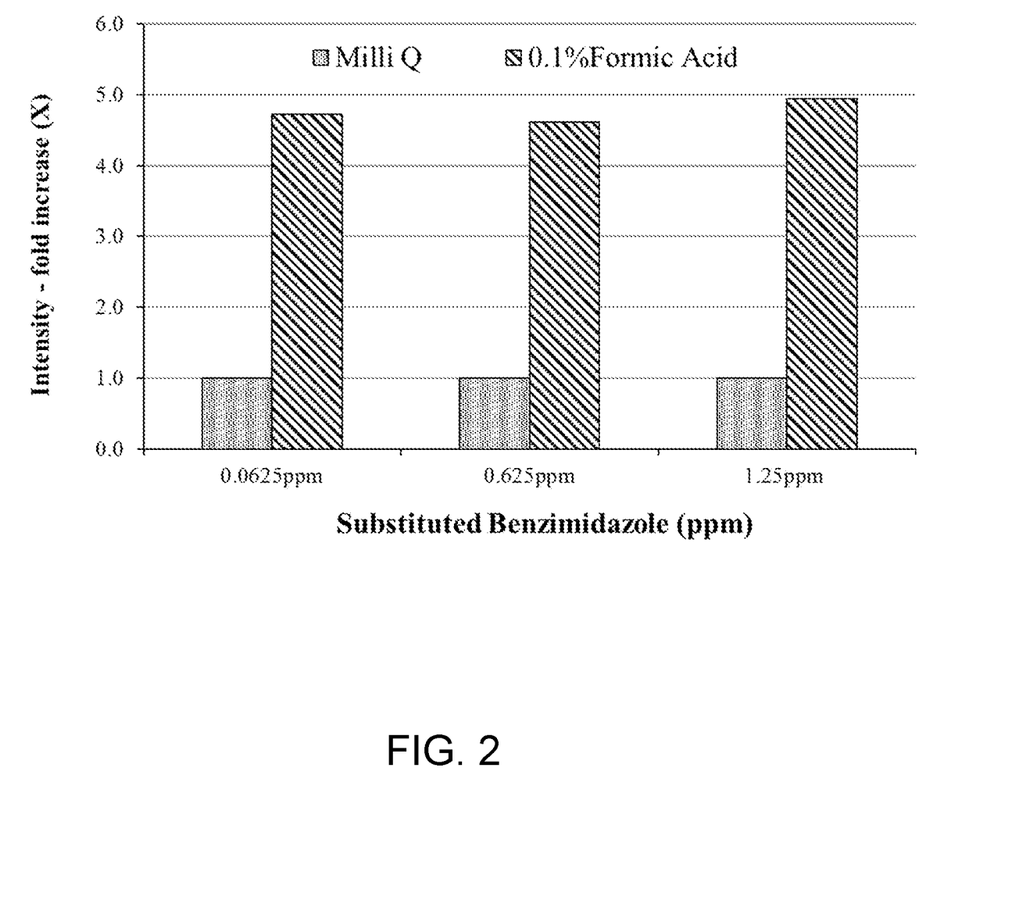
FIG. 2 shows the effects of formic acid on the fluorescence intensity of the benzimidazole-based compound.

FIG. 2 shows the effects of formic acid on the fluorescence intensity at different concentrations of the substituted benzimidazole. When about 0.1% by weight of formic acid was added to the samples, a significant increase in fluorescence was detected in the emission band range of 350 to 370 nm.

Example 2

To reduce the interference effects of hard water, a simple sample preparation protocol was developed where samples were diluted to a minimum of about 10 times using pure water. Dilution of the sample decreased interference caused by cooling water components while fluorescence intensity was high enough to quantify the substituted benzimidazole. As the fluorescence intensity of the substituted benzimidazole is strong (approx. 1 ppm=$10^7$ cps), it can be detected with good confidence even on 10 times dilution of the sample.

Figure 3:
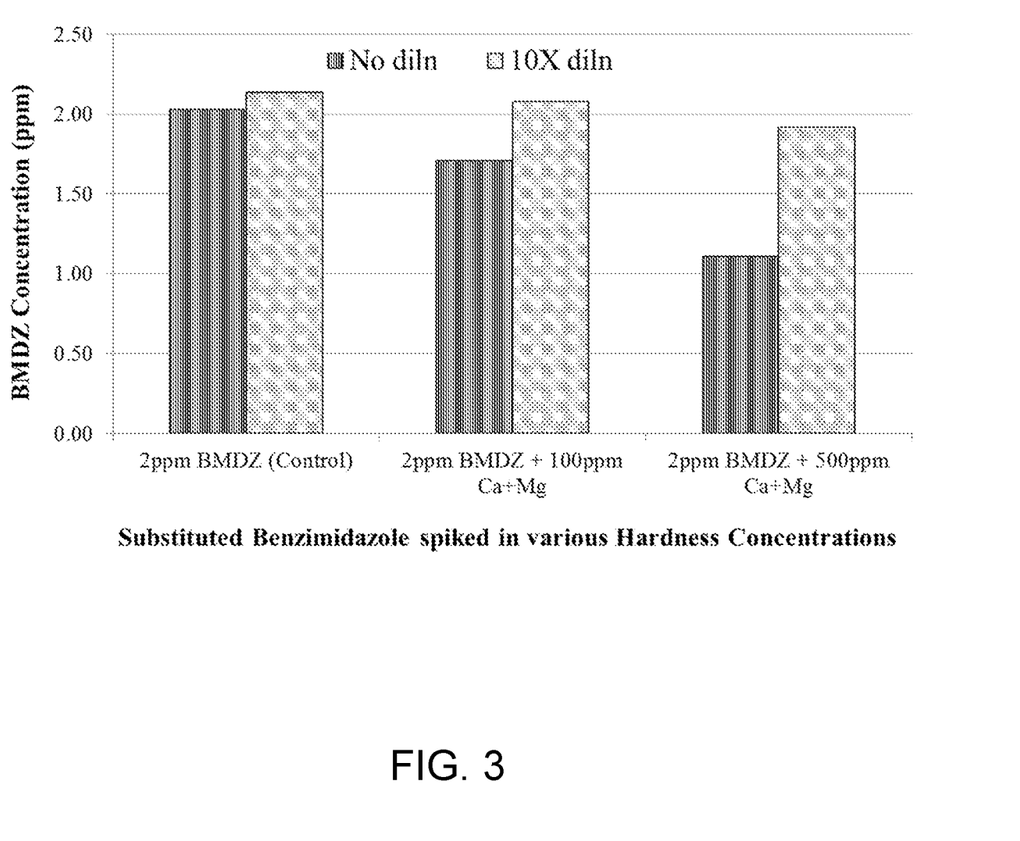
FIG. 3 shows the effects of hard water on 2 ppm of the benzimidazole-based compound.

Hardness solutions of two different concentrations (50 ppm Ca+50 ppm Mg and 250 ppm Ca+250 ppm Mg) were prepared and spiked with 2 ppm of the substituted benzimidazole. Then solution was acidified with 0.1% formic acid. Control solution (without hardness) containing 2 ppm of the substituted benzimidazole and acidified with 0.1% by weight with formic acid was also prepared. The fluorometer settings were the same as described in Example 1. FIG. 3 shows the effects of hard water on 2 ppm of the substituted benzimidazole. FIG. 3 also shows fluorescence intensity of the substituted benzimidazole with and without sample dilution in presence of interferences coming from cooling water.

It was observed that the samples containing Ca and Mg ions reduced the recoveries of the substituted benzimidazole. However, when these samples were diluted 10 times using 0.1% formic acid and then measured on the fluorometer, good recoveries were obtained for the substituted benzimidazole and the interference of Ca and Mg was reduced significantly.

Example 3

Figure 4:
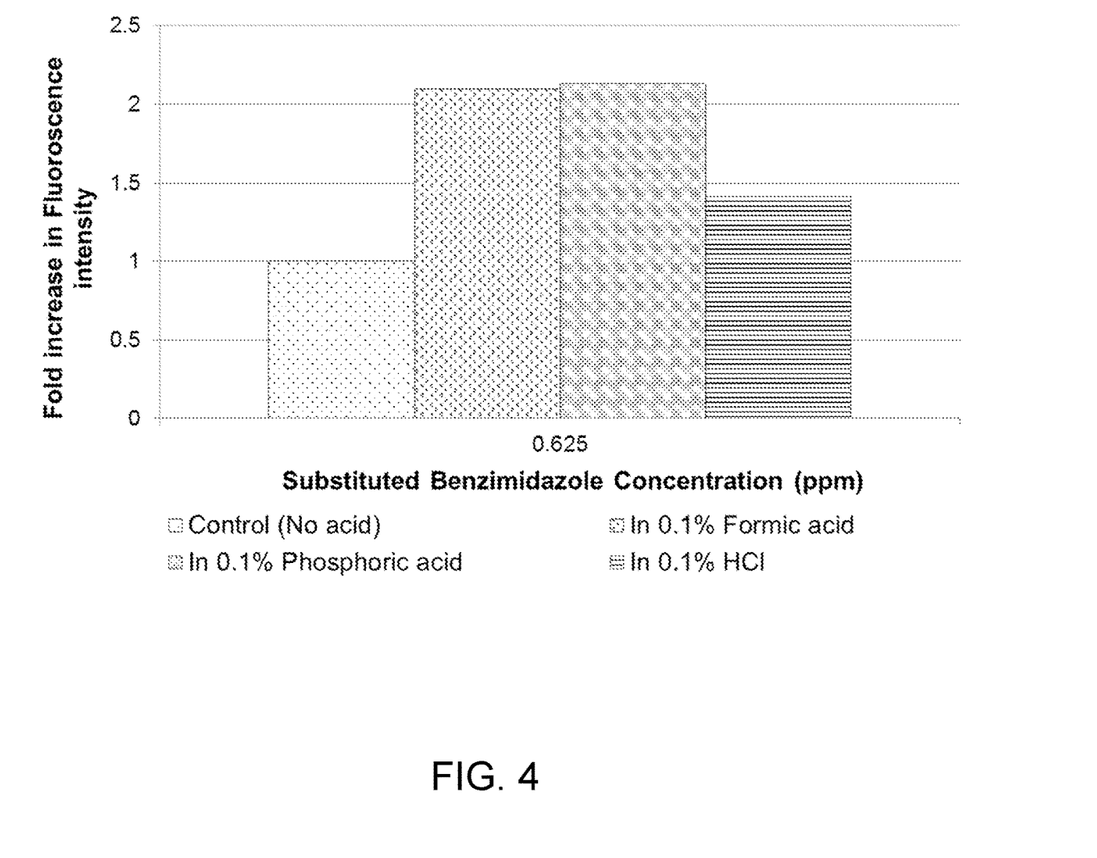
FIG. 4 shows the effects of acidification by formic acid, phosphoric acid, and hydrochloric acid on the fluorescence intensity of the benzimidazole-based compound.

Several different acids, including hydrochloric acid, formic acid, and phosphoric acid, were studied for their effect on fluorescence intensity of the substituted benzimidazole (FIG. 4). The percentages shown in FIG. 4 are weight percentages. It was found that all of the studied acids showed about similar increased fluorescence intensity with increased concentration of formic acid for the 370 nm emission band.

Compound structures and chemical names were prepared and determined using ChemDraw Professional version 15.1.

Any composition disclosed herein may comprise, consist of, or consist essentially of any of the compounds/components disclosed herein. In accordance with the present disclosure, the phrases "consist essentially of," "consists essentially of," "consisting essentially of," and the like limit the scope of a claim to the specified materials or steps and those materials or steps that do not materially affect the basic and novel characteristic(s) of the claimed invention.

As used herein, the term "about" refers to the cited value being within the errors arising from the standard deviation found in their respective testing measurements, and if those errors cannot be determined, then "about" refers to within 10% of the cited value.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a compound" is intended to include "at least one compound" or "one or more compounds."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A method of determining corrosion inhibitor concentration in water, comprising the steps of:
    withdrawing a sample of water from an aqueous system, wherein the sample of water is hard water and the sample of water comprises a benzimidazole-based corrosion-inhibitor compound;
    diluting the sample of water by adding water to the sample of water, thereby providing a diluted sample of water;
    adding an acid to the diluted sample of water, thereby providing an acidified sample of water having a pH of about 1 to about 5;
    exposing the acidified sample of water to light energy of a selected excitation wavelength;
    measuring an intensity of emitted light about a selected fluorescence emission wavelength;
    comparing the intensity of the emitted light to a standard curve, the standard curve comprising a plot of fluorescence emission intensity of the benzimidazole-based corrosion-inhibitor compound versus concentration of the benzimidazole-based corrosion-inhibitor compound; and
    determining the concentration of the benzimidazole-based corrosion-inhibitor compound in the acidified sample of water from the standard curve.

2. The method of claim 1, wherein the sample of water from the aqueous system is diluted by about 10 times.

3. The method of claim 1, wherein the aqueous system is a cooling water system and the sample of water from the aqueous system is a sample of cooling tower water.

4. The method of claim 1, wherein the sample of water from the aqueous system comprises about 25 ppm to about 400 ppm of calcium and about 25 ppm to about 400 ppm of magnesium.

5. The method of claim 1, wherein the benzimidazole-based corrosion-inhibitor compound is of formula (I) or salt thereof, where R¹ is halo, hydrogen, deuterium, hydroxyl, carbonyl, substituted or unsubstituted $C_1$-$C_{16}$ alkyl, substituted or unsubstituted $C_6$ aryl, substituted or unsubstituted $C_2$-$C_{16}$ alkenyl, substituted or unsubstituted $C_2$-$C_{16}$ alkynyl, substituted or unsubstituted $C_4$-$C_6$ heteroaryl, or substituted or unsubstituted $C_3$-$C_8$ cycloalkyl;

X is hydrogen or $CR^2R^3Y$;

Y is hydroxyl, halo, oxo, substituted or unsubstituted $C_1$-$C_{16}$ alkoxy, thiol, alkylthio, amino, hydrogen, or aminoalkyl;

$R^2$ and $R^3$ are each independently selected from the group consisting of: hydrogen, halo, hydroxyl, substituted or unsubstituted $C_6$ aryl, substituted or unsubstituted $C_4$-$C_6$ heteroaryl, carbonyl, substituted or unsubstituted $C_2$-$C_{16}$ alkenyl, substituted or unsubstituted $C_2$-$C_{16}$ alkynyl, substituted or unsubstituted $C_3$-$C_8$ cycloalkyl, and substituted or unsubstituted $C_1$-$C_{16}$ alkyl; and $R^4$, $R^5$, $R^6$, and $R^7$ are each independently selected from the group consisting of: hydrogen, halo, amino, cyano, substituted or unsubstituted $C_1$-$C_{16}$ alkoxy, hydroxyl, thiol, carbonyl, nitro, phosphoryl, phosphonyl, sulfonyl, substituted or unsubstituted $C_1$-$C_{16}$ alkyl, substituted or unsubstituted $C_6$ aryl, substituted or unsubstituted $C_2$-$C_{16}$ alkenyl, substituted or unsubstituted $C_2$-$C_{16}$ alkynyl, substituted or unsubstituted $C_4$-$C_6$ heteroaryl, and substituted or unsubstituted $C_3$-$C_8$ cycloalkyl.

6. The method of claim 1, wherein the benzimidazole-based corrosion-inhibitor compound is of formula (II) or salt thereof, (II)

where R¹ is hydrogen, a substituted or unsubstituted $C_1$-$C_{16}$ alkyl group, or a substituted or unsubstituted $C_6$ aryl group;

$R^4$, $R^5$, $R^6$, and $R^7$ are each independently selected from the group consisting of:

hydrogen, halo, amino, cyano, substituted or unsubstituted $C_1$-$C_{16}$ alkoxy, hydroxyl, thiol, carbonyl, nitro, phosphoryl, phosphonyl, sulfonyl, substituted or unsubstituted $C_1$-$C_{16}$ alkyl, substituted or unsubstituted $C_6$ aryl, substituted or unsubstituted $C_2$-$C_{16}$ alkenyl, substituted or unsubstituted $C_2$-$C_{16}$ alkynyl, substituted or unsubstituted $C_4$-$C_6$ heteroaryl, and substituted or unsubstituted $C_3$-$C_8$ cycloalkyl;

$R^8$ is a bond or $CHR^9$;

$R^9$ is hydrogen, halo, $NR^{10}R^{11}$, or $OR^{10}$;

wherein $R^{10}$ and $R^{11}$ are each independently selected from the group consisting of: hydrogen, a substituted or unsubstituted $C_1$-$C_{16}$ alkyl group, and a substituted or unsubstituted $C_6$ aryl group; and each Z is independently nitrogen, $CR^4$, or $N^+R^{10}$; provided that at least four of Z are $CR^4$.

7. The method of claim 6, wherein each Z is $CR^4$ and $R^4$ is hydrogen.

8. The method of claim 1, wherein the benzimidazole-based corrosion-inhibitor compound is selected from the group consisting of:

9. The method of claim 1, wherein the acid is a mineral acid, an organic acid, or any combination thereof.

10. The method of claim 1, wherein the acid is hydrochloric acid, formic acid, phosphoric acid, nitric acid, sulfuric acid, acetic acid, propionic acid, oxalic acid, lactic acid, citric acid or any combination thereof.

11. The method of claim 1, wherein the selected excitation wavelength is from about 200 nm to about 400 nm.

12. The method of claim 1, wherein the selected fluorescence emission wavelength is from about 300 nm to about 500 nm.

13. The method of claim 1, wherein the benzimidazole-based corrosion-inhibitor compound is protonated after adding the acid.

14. The method of claim 1, wherein the acid is added to the diluted sample of water in an amount of about 0.001% by weight to about 10% by weight.

15. A method of controlling the concentration of a corrosion inhibitor in an aqueous system, comprising:

determining the concentration of the benzimidazole-based corrosion-inhibitor compound in the acidified sample of water according to claim 1;

determining the concentration of the benzimidazole-based corrosion-inhibitor compound in the sample of water from the aqueous system; and adding the benzimidazole-based corrosion-inhibitor compound to the aqueous system if the concentration of the benzimidazole-based corrosion-inhibitor compound in the sample of water from the aqueous system is below a predetermined level.

16. The method of claim 15, wherein the predetermined level is from about 0.05 ppm to about 20 ppm.

17. A method of determining corrosion inhibitor concentration in water, comprising the steps of:

withdrawing a sample of water from an aqueous system, wherein the sample of water is hard water and the sample of water comprises a benzimidazole-based corrosion-inhibitor compound;

adding an acid to the sample of water, thereby providing an acidified sample of water having a pH of about 1 to about 5;

diluting the acidified sample of water by adding water to the acidified sample of water, thereby providing a diluted sample of water;

exposing the diluted sample of water to light energy of a selected excitation wavelength;

measuring an intensity of emitted light about a selected fluorescence emission wavelength;

comparing the intensity of the emitted light to a standard curve, the standard curve comprising a plot of fluorescence emission intensity of the benzimidazole-based corrosion-inhibitor compound versus concentration of the benzimidazole-based corrosion-inhibitor compound; and determining the concentration of the benzimidazole-based corrosion-inhibitor compound in the diluted sample of water from the standard curve.

18. The method of claim 17, wherein the acidified sample of water is diluted by about 10 times.

19. The method of claim 17, wherein the aqueous system is a cooling water system and the sample of water from the aqueous system is a sample of cooling tower water.

20. A method of controlling the concentration of a corrosion inhibitor in an aqueous system, comprising:

determining the concentration of the benzimidazole-based corrosion-inhibitor compound in the diluted sample of water according to claim 17;

determining the concentration of the benzimidazole-based corrosion-inhibitor compound in the sample of water from the aqueous system; and adding the benzimidazole-based corrosion-inhibitor compound to the aqueous system if the concentration of the benzimidazole-based corrosion-inhibitor compound in the sample of water from the aqueous system is below a predetermined level.

* * * * *